(12) United States Patent
El Hija

(10) Patent No.: US 9,662,361 B1
(45) Date of Patent: May 30, 2017

(54) METHOD FOR TREATING AZOOSPERMIA

(71) Applicant: Mahmoud Abu El Hija, Wappingers Falls, NY (US)

(72) Inventor: Mahmoud Abu El Hija, Wappingers Falls, NY (US)

( * ) Notice: Subject to any disclaimer, the term of this patent is extended or adjusted under 35 U.S.C. 154(b) by 0 days.

(21) Appl. No.: 15/198,160

(22) Filed: Jun. 30, 2016

(51) Int. Cl.

| | | |
|---|---|---|
| *A61K 36/00* | (2006.01) |
| *A61K 36/484* | (2006.01) |
| *A61K 36/258* | (2006.01) |
| *A61K 36/31* | (2006.01) |
| *A61K 36/296* | (2006.01) |
| *A61K 36/185* | (2006.01) |
| *A61K 36/16* | (2006.01) |
| *A61K 36/87* | (2006.01) |
| *A61K 31/375* | (2006.01) |
| *A61K 36/48* | (2006.01) |
| *A61K 31/015* | (2006.01) |
| *A61K 31/355* | (2006.01) |
| *A61K 31/51* | (2006.01) |
| *A61K 31/525* | (2006.01) |
| *A61K 31/555* | (2006.01) |
| *A61K 31/455* | (2006.01) |
| *A61K 31/197* | (2006.01) |
| *A61K 31/519* | (2006.01) |
| *A61K 31/593* | (2006.01) |
| *A61K 31/675* | (2006.01) |
| *A61K 33/18* | (2006.01) |
| *A61K 31/19* | (2006.01) |
| *A61K 33/14* | (2006.01) |
| *A61K 31/191* | (2006.01) |

(52) U.S. Cl.
CPC .......... *A61K 36/484* (2013.01); *A61K 31/015* (2013.01); *A61K 31/19* (2013.01); *A61K 31/191* (2013.01); *A61K 31/197* (2013.01); *A61K 31/355* (2013.01); *A61K 31/375* (2013.01); *A61K 31/455* (2013.01); *A61K 31/51* (2013.01); *A61K 31/519* (2013.01); *A61K 31/525* (2013.01); *A61K 31/555* (2013.01); *A61K 31/593* (2013.01); *A61K 31/675* (2013.01); *A61K 33/14* (2013.01); *A61K 33/18* (2013.01); *A61K 36/16* (2013.01); *A61K 36/185* (2013.01); *A61K 36/258* (2013.01); *A61K 36/296* (2013.01); *A61K 36/31* (2013.01); *A61K 36/48* (2013.01); *A61K 36/87* (2013.01)

(58) Field of Classification Search
None
See application file for complete search history.

*Primary Examiner* — Qiuwen Mi

(57) ABSTRACT

A method for treating azoospermia consists of lowering a patient's testosterone for an extended duration in order to induce spermatogonia stem cell function to produce spermatozoa. The patient's testosterone is reduced through the incorporation of *glycyrrhiza glabra* in three medicinal mixtures. A first medicinal mixture is used to lower testosterone in the patient as the first medicinal mixture is primarily *glycyrrhiza glabra*, and the first medicinal mixture is administered for at least one month. The quantity of *glycyrrhiza glabra* is reduced in administration of the second medicinal mixture over at least two months, subsequent to the first medicinal mixture. The quantity of *glycyrrhiza glabra* is further reduced in administration of the third medicinal mixture over at least three months, subsequent to the second medicinal mixture. A plurality of additional ingredients is included in the second medicinal mixture and the third medicinal mixture in order to promote spermatozoa production and virility.

15 Claims, 7 Drawing Sheets

Glycyrrhiza Glabra

First Medicinal Mixture

FIG. 3

| Glycyrrhiza Glabra | Red Panax Ginseng |
|---|---|
| Pomegranate | Maca |
| Tribulus Terrestris | Horny Goat Weed |
| Mucuna Pruriens | Damiana Leaf |
| Ginkgo Biloba | Grape Seed Extract |
| Vitamin C | Additional Vitamin Supplements |
| Additional Dietary Supplements | |

Third Medicinal Mixture

FIG. 6

METHOD FOR TREATING AZOOSPERMIA

FIELD OF THE INVENTION

The present invention relates generally to a method of treating a medical condition. More specifically, the present invention relates to a method for treating azoospermia through the administration of *glycyrrhiza glabra* to a patient.

BACKGROUND OF THE INVENTION

Azoospermia is a medical condition where there is no measureable level of sperm within the semen for a male. Azoospermia can manifest in three major types: pre-testicular azoospermia, testicular azoospermia, and post-testicular azoospermia. Pre-testicular azoospermia can be characterized inadequate stimulation of otherwise normal testicles and genital tract. Typically, follicle-stimulating hormone (FSH) levels are low with inadequate stimulation of the testes to produce sperm. Testicular azoospermia is a specific case where the testes are abnormal, atrophic, or absent, and the production of sperm is severely disturbed to absent. FSH levels are elevated due to diminished feedback responses to inhibit FSH. Post-testicular azoospermia is a specific condition where sperm is produced but not ejaculated. The post-testicular azoospermia condition is usually caused by a physical obstruction, most commonly a vasectomy.

The present invention is a method for treating azoospermia where a medicinal mixture including *glycyrrhiza glabra*, an extract of licorice root, is administered to a male patient. Through administration a medicinal mixture, the present invention restores the sperm count in semen or enhances the success chance of sperm retrieval over an administration period.

BRIEF DESCRIPTION OF THE DRAWINGS

FIG. 3 is a box diagram detailing the ingredients of the first medicinal mixture.

FIG. 6 is a box diagram detailing the ingredients of the third medicinal mixture.

DETAIL DESCRIPTIONS OF THE INVENTION

All illustrations of the drawings are for the purpose of describing selected versions of the present invention and are not intended to limit the scope of the present invention.

The present invention is a method for treating azoospermia, a medical condition where a male patient does not have a measureable sperm count in the patient's semen. The present invention is performed over the course of several months in order to restore the sperm count in semen or enhances the success of sperm retrieval. Therefore, the present invention increases the fertility of male patients with azoospermia. A number of ingredients are required in order to perform the method of treating azoospermia, including a quantity of *glycyrrhiza glabra*, a quantity of red *panax ginseng*, a quantity of pomegranate, a quantity of maca, a quantity of *tribulus terrestris*, a quantity of horny goat weed, a quantity of *mucuna pruriens*, a quantity of damiana leaf, a quantity of *ginkgo biloba*, a quantity of grape seed extract, and a quantity of vitamin C.

These ingredients are combined into three separate medicinal mixtures in order to temporarily suppress testosterone in the male patient and restore testosterone levels to normal gradually over time. In accordance to FIG. 1, a first portion of the quantity of *glycyrrhiza glabra* is heterogeneously mixed into a first medicinal mixture. *Glycyrrhiza glabra*, commonly known as licorice root, is the primary ingredient for lowering testosterone. The first medicinal mixture is administered daily to a patient for at least one month. The first medicinal mixture is preferred to be a mass quantity between 10 milligrams (mg) and 1 gram (g), as detailed in FIG. 2. In accordance to Table 1, the first portion of *glycyrrhiza glabra* is at least 96% by weight (wt %) of the first medicinal mixture. Administrating the first medicinal mixture at this composition and this mass quantity reduces the testosterone levels in human blood and induces the spermatogonia stem cell in order to produce spermatozoa over the administration duration.

TABLE 1

| First Medicinal Mixture | |
| --- | --- |
| Component | Minimum percent by weight (wt %) |
| Glycyrrhiza Glabra | 96% |

Figure 1:
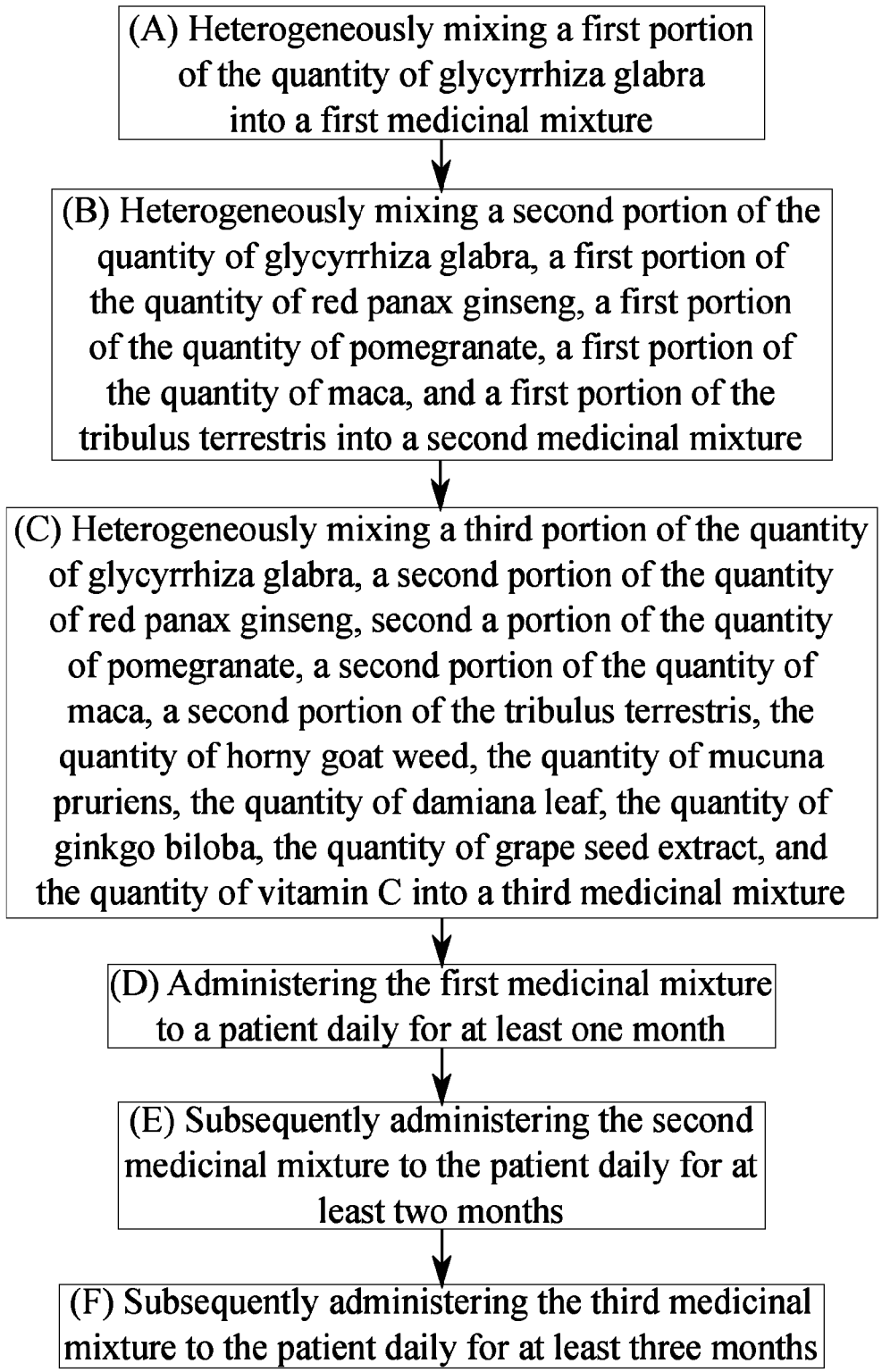
FIG. 1 is a flow diagram for the present invention.
Figure 4:
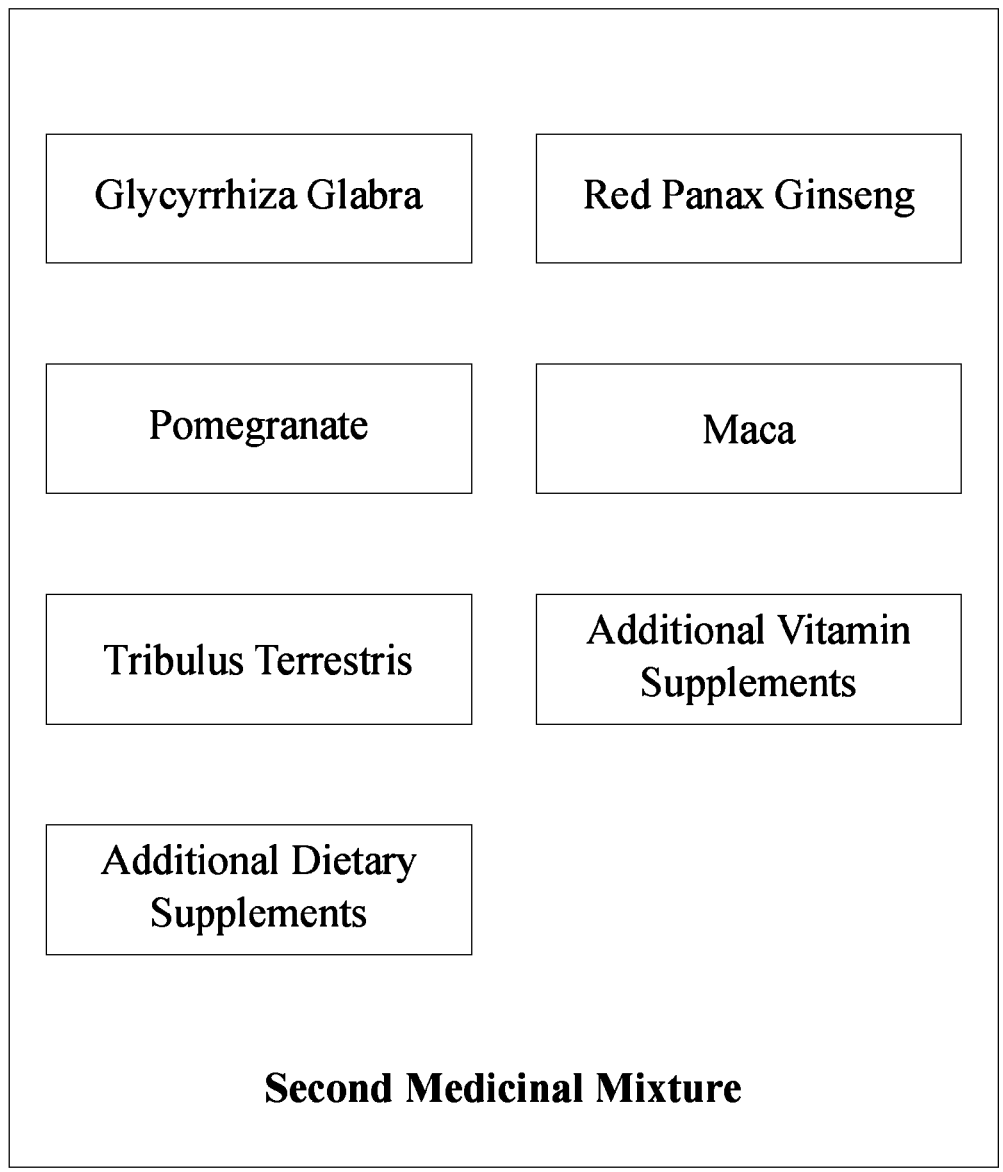
FIG. 4 is a box diagram detailing the ingredients of the second medicinal mixture.

In accordance to FIG. 1 and FIG. 4, a second portion of the quantity of *glycyrrhiza glabra*, a first portion of the quantity of red *panax ginseng*, a first portion of the quantity of pomegranate, a first portion of the quantity of maca, and a first portion of the *tribulus terrestris* are heterogeneously mixed into a second medicinal mixture. In addition to the *glycyrrhiza glabra*, the red *panax ginseng* assists in the treatment of azoospermia by inducing the differentiation of the spermatogonia stem cells. The pomegranate, maca, and *tribulus terrestris* support testicular function and help produce sperm. In accordance to FIG. 1, the second medicinal mixture is administered daily to the patient for at least two months, subsequent to the administration of the first medicinal mixture. The second medicinal mixture is preferred administered as a mass quantity between 10 mg and 1 g, as detailed in FIG. 2. In accordance to Table 2, the preferred composition for the second medicinal mixture is as follows: the second portion of the quantity of *glycyrrhiza glabra* is at least 60 wt % of the second medicinal mixture; the first quantity of red *panax ginseng* is at least 3 wt % of the second medicinal mixture; the first portion of the quantity of pomegranate is at least 10 wt % of the second medicinal mixture; the first portion of the quantity of maca is at least 3 wt % of the second medicinal mixture; and the first portion of the *tribulus terrestris* is at least 3 wt % of the second medicinal mixture. The second portion of quantity of *glycyrrhiza glabra* in the second medicinal mixture is reduced from the first portion of the quantity of *glycyrrhiza glabra* in the first medicinal mixture in order to begin restoring testosterone to naturally occurring levels gradually. The remainder of the composition provides sufficient beneficial properties including: inducing the differentiation of spermatogonia from the red *panax ginseng*; improving sperm quality and increasing sex drive from the pomegranate; increasing sperm count through the maca; and increasing virility from the *tribulus terrestris* without affecting testosterone levels.

TABLE 2

Second Medicinal Mixture

| Component | Minimum percent by weight (wt %) |
|---|---|
| Glycyrrhiza Glabra | 60% |
| Red Panax Ginseng | 3% |
| Pomegranate | 10% |
| Maca | 3% |
| Tribulus Terrestris | 3% |
| Additional Vitamin Supplements | |
| Beta Carotene | 0.07% |
| D-Alpha Tocopheryl Succinate | 0.1% |
| Thiamin | 0.07% |
| Riboflavin | 0.05% |
| Methylcobalamin | 0.05% |
| Nicotinamide | 0.5% |
| Pantothenic Acid | 0.05% |
| Folic Acid | 0.03% |
| Additional Dietary Supplements | |
| Potassium Iodide | 0.14% |
| Calcium Carbonate | 0.22% |
| Magnesium Hydroxide | 0.45% |
| Magnesium Gluconate | 0.18% |

Figure 2:
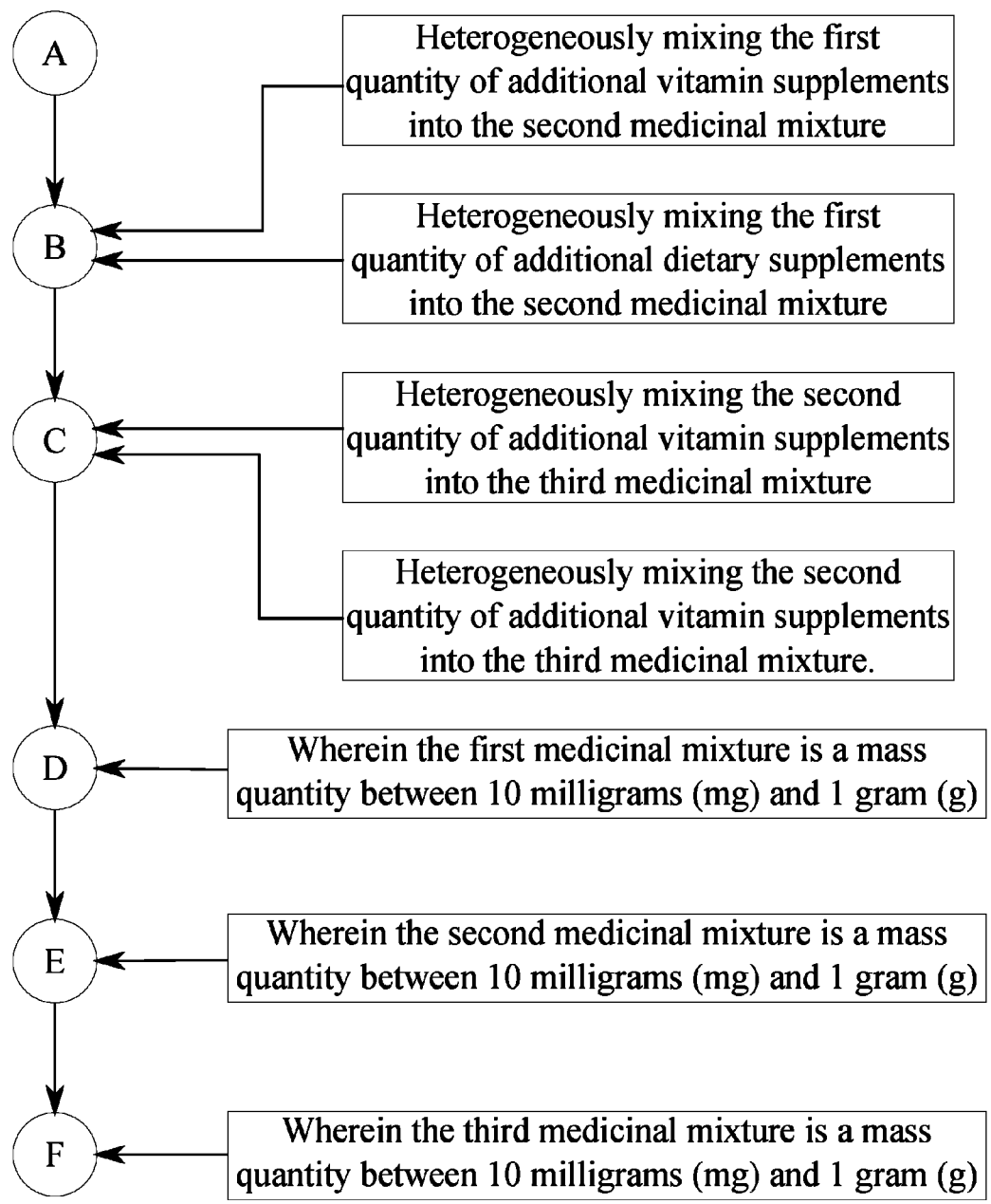
FIG. 2 is a flow diagram for the present invention detailing: the mass quantity for the first medicinal mixture, the second medicinal mixture and the third medicinal mixture; the heterogeneous mixing of the first quantity of additional vitamin supplements and the first quantity of dietary supplements into the second medicinal mixture; and the heterogeneous mixing of the second quantity of additional vitamin supplements and the second quantity of dietary supplements into the third medicinal mixture.
Figure 5:
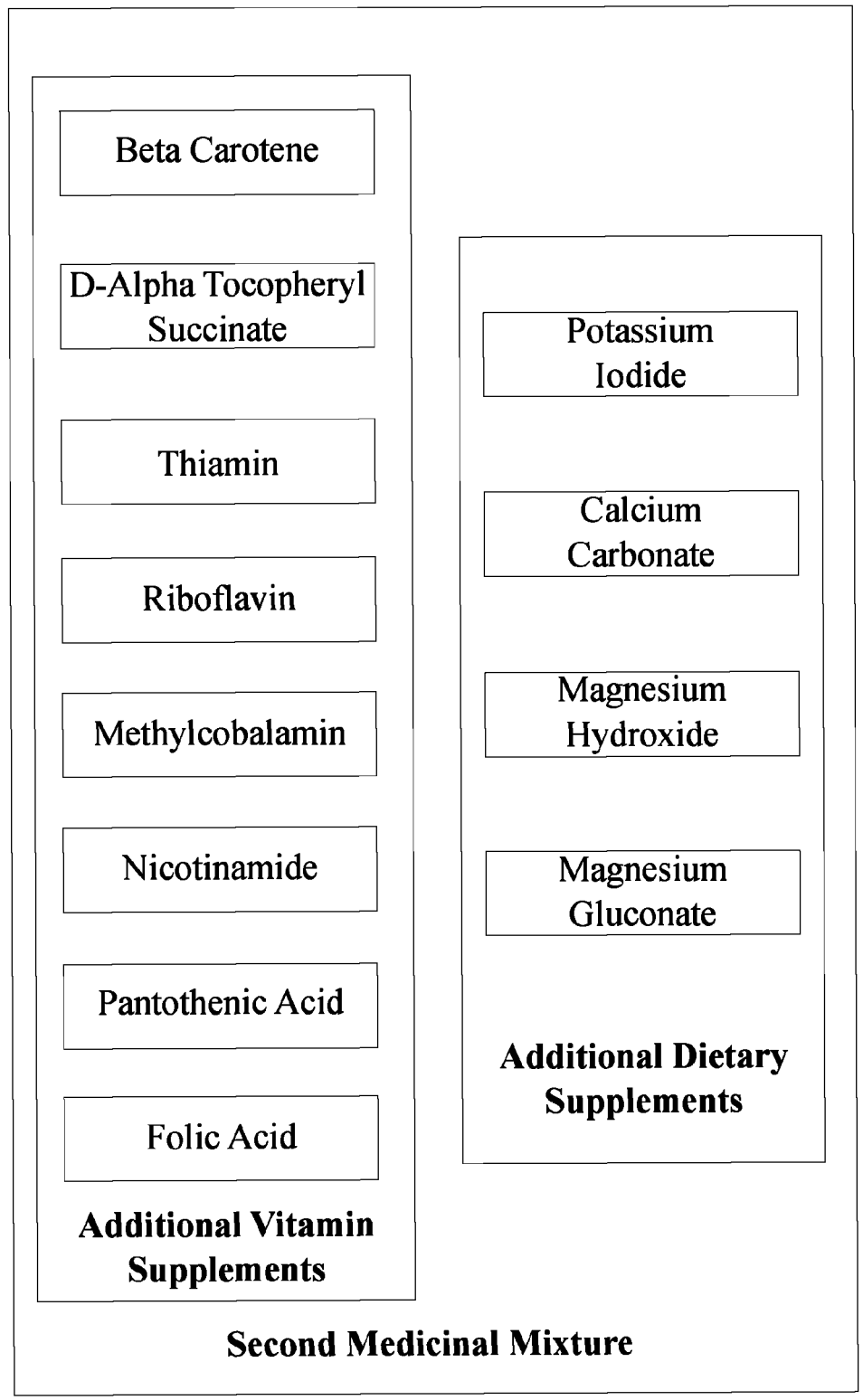
FIG. 5 is a box diagram detailing further ingredients for the first quantity of additional vitamin supplements and the first quantity of dietary supplements of the second medicinal mixture.

In some embodiments of the present invention, a first quantity of additional vitamin supplements is heterogeneously mixed into the second medicinal mixture, in accordance to FIG. 2. As shown in FIG. 5, the first quantity of additional vitamin supplements is selected from a group consisting of: a quantity of beta carotene, a quantity of d-alpha tocopheryl succinate, a quantity of thiamin, a quantity of riboflavin, a quantity of methylcobalamin, a quantity of nicotinamide, a quantity of pantothenic acid, a quantity of folic acid, and combinations thereof. The first quantity of additional vitamin supplements provides essential nutrients to be metabolized by the patient. In one embodiment of the present invention, the first quantity of additional vitamin supplements is a combination of the quantity of beta carotene, the quantity of d-alpha tocopheryl succinate, the quantity of thiamin, the quantity of riboflavin, the quantity of methylcobalamin, the quantity of nicotinamide, the quantity of pantothenic acid, and the quantity of folic acid. In accordance to Table 2, the preferred composition for the first quantity of additional vitamin supplements is as follows: the quantity of beta carotene is approximately 0.07% of the second medicinal mixture; the quantity of d-alpha tocopheryl succinate is approximately 0.1% of the second medicinal mixture; the quantity of thiamin is approximately 0.07% of the second medicinal mixture; the quantity of riboflavin is approximately 0.05% of the second medicinal mixture; the quantity of methylcobalamin is approximately 0.05% of the second medicinal mixture; the quantity of nicotinamide is approximately 0.5% of the second medicinal mixture; the quantity of pantothenic acid is approximately 0.05% of the second medicinal mixture; and the quantity of folic acid is approximately 0.03% of the second medicinal mixture. This composition provides these ingredients of the first quantity of additional vitamin supplements in sufficient quantity to be beneficial to the patient over the administration period for the second medicinal mixture.

In some embodiments of the present invention, a first quantity of additional dietary supplements is heterogeneously mixed into the second medicinal mixture, as detailed in FIG. 2. In accordance to FIG. 5, the first quantity of additional dietary supplements is selected from a group consisting of: a quantity of potassium iodide, a quantity of calcium carbonate, a quantity of magnesium hydroxide, a quantity of magnesium gluconate, and combinations thereof. Similar to the first quantity of additional vitamin supplements, the first quantity of additional dietary supplements provides essential nutrients to be metabolized by the patient. In one embodiment of the present invention, the first quantity of additional dietary supplements is a combination of the quantity of potassium iodide, the quantity of calcium carbonate, the quantity of magnesium hydroxide, and the quantity of magnesium gluconate. In accordance to Table 2, the composition for the first additional dietary supplement is as follows: the quantity of potassium iodide being approximately 0.14% of the second medicinal mixture; the quantity of calcium carbonate being approximately 0.22% of the second medicinal mixture; the quantity of magnesium hydroxide being approximately 0.45% of the second medicinal mixture; and the quantity of magnesium gluconate being approximately 0.18% of the second medicinal mixture. This composition provides these ingredients for the first quantity of dietary supplements in sufficient amount to be beneficial to the patient over the administration period for the second medicinal mixture.

In accordance to FIG. 1 and FIG. 6, a third portion of the quantity of *glycyrrhiza glabra*, a second portion of the quantity of red *panax ginseng*, a second portion of the quantity of pomegranate, a second portion of the quantity of maca, a second portion of the *tribulus terrestris*, the quantity of horny goat weed, the quantity of *mucuna pruriens*, the quantity of damiana leaf, the quantity of *ginkgo biloba*, the quantity of grape seed extract, and the quantity of vitamin C are heterogeneously mixed into a third medicinal mixture. The *glycyrrhiza glabra*, the red *panax ginseng*, the pomegranate, the maca, and the quantity of *tribulus terrestris* provide the same beneficial properties as described for the second medicinal mixture. The horny goat weed imparts properties to help erectile dysfunction and involuntary ejaculation to the third medicinal mixture. The *mucuna pruriens* improves sexual behavior, libido, and potency. The damiana leaf improves sexual satisfaction and orgasm frequency. The *ginkgo biloba* assists in improving sexual satisfaction and assuaging sexual dysfunction. The grape seed extract helps to promote circulation of blood in the patient. The vitamin C promotes general health of the patient.

In accordance to FIG. 1, the third medicinal mixture is administered daily to the patient for at least three months, subsequent to the administration of the second medicinal mixture. The third medicinal mixture is preferred to be administered as a mass quantity between 10 mg and 1 g, as detailed in FIG. 2. In accordance to Table 3, the preferred composition for the third medicinal mixture is as follows: the third portion of the quantity of *glycyrrhiza glabra* is at least 10 wt % of the third medicinal mixture; the second portion of the quantity of red *panax ginseng* is at least 3 wt % of the third medicinal mixture; the second portion of the quantity of pomegranate is at least 5 wt % of the third medicinal mixture; the second portion of the quantity of maca is at least 10 wt % of the third medicinal mixture; the second portion of the *tribulus terrestris* is at least 3 wt % of the third medicinal mixture; the quantity of horny goat weed mixture is at least 5 wt % of the third medicinal mixture; the quantity of *mucuna pruriens* is at least 5 wt % of the third medicinal mixture; the quantity of damiana leaf is at least 5 wt % of the third medicinal mixture; the quantity of *ginkgo biloba* is at least 6 wt % of the third medicinal mixture; the quantity of grape seed extract is at least 10 wt % of the third medicinal mixture; and the quantity of vitamin C is at least 15 wt % of the third medicinal mixture. The third portion of quantity of *glycyrrhiza glabra* in the third medicinal mixture is further reduced from the second portion of the quantity of *glycyrrhiza glabra* in the second medicinal mixture in order to continue restoring testosterone to naturally occurring levels gradually. The composition for the third medicinal mixture allows for an effective quantity for each of the ingredients of the third medicinal mixture to impart the beneficial aforementioned properties to the patient.

TABLE 3

Third Medicinal Mixture

| Component | Minimum percent by weight (wt %) |
| --- | --- |
| Glycyrrhiza Glabra | 10% |
| Red Panax Ginseng | 3% |
| Pomegranate | 5% |
| Maca | 10% |
| Tribulus Terrestris | 3% |
| Horny Goat Weed | 5% |
| Mucuna Pruriens | 5% |
| Damiana Leaf | 5% |
| Ginkgo Biloba | 6% |
| Grape Seed Extract | 10% |
| Vitamin C | 15% |
| Additional Vitamin Supplements | |
| Beta Carotene | 0.4% |
| D-Alpha Tocopheryl Succinate | 1.4% |
| Thiamin | 0.7% |
| Riboflavin | 0.2% |
| Methylcobalamin | 0.12% |
| Nicotinamide | 1.34% |
| Pantothenic Acid | 0.2% |
| Folic Acid | 0.04% |
| Vitamin D3 | 0.5% |
| Pyridoxal 5-Phosphate | 0.08% |
| Additional Dietary Supplements | |
| Potassium Iodide | 0.27% |
| Calcium Carbonate | 3.1% |
| Magnesium Hydroxide | 3.8% |
| Magnesium Gluconate | 0.62% |
| Copper Gluconate | 0.08% |
| Zinc Sulfate | 1.35% |
| L-Arginine | 1.55% |

In some embodiments of the present invention, a second quantity of additional vitamin supplements is heterogeneously mixed into the third medicinal mixture, as shown in FIG. 2. In accordance to FIG. 7, the second quantity of additional vitamin supplements is selected from a group consisting of: a quantity of beta carotene, a quantity of d-alpha tocopheryl succinate, a quantity of thiamin, a quantity of riboflavin, a quantity of methylcobalamin, a quantity of nicotinamide, a quantity of pantothenic acid, a quantity of folic acid, a quantity of vitamin D3, a quantity of pyridoxal 5-phosphate, and combinations thereof. Similar to the first quantity of additional vitamin supplements, the second quantity of additional vitamin supplements provides essential nutrients to be metabolized by the patient.

Figure 7:
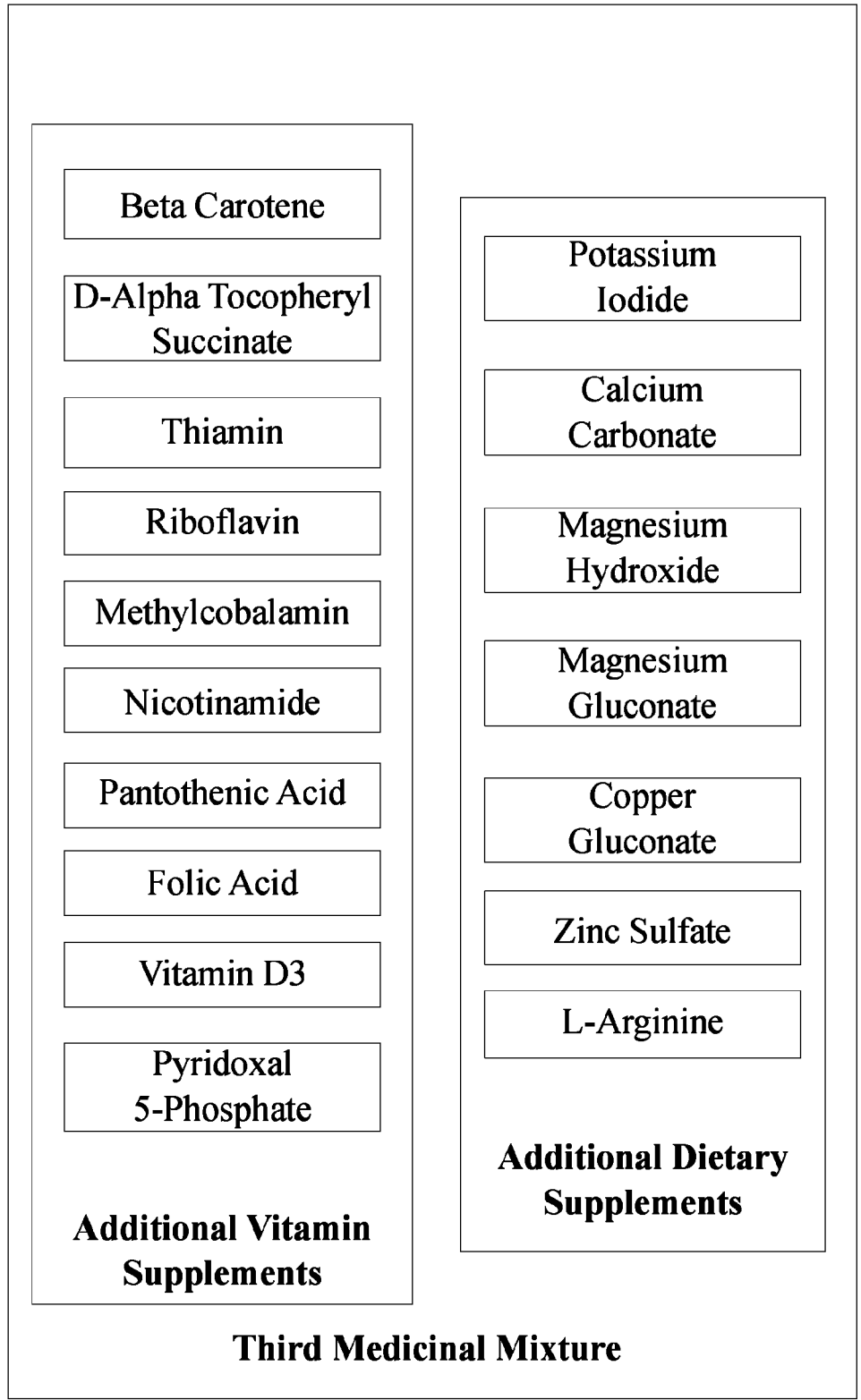
FIG. 7 is a box diagram detailing further ingredients for the second quantity of additional vitamin supplements and the second quantity of dietary supplements of the third medicinal mixture.

In one embodiment of the present invention, the second quantity of additional vitamin supplements is a combination of the quantity of beta carotene, the quantity of d-alpha tocopheryl succinate, the quantity of thiamin, the quantity of riboflavin, the quantity of methylcobalamin, the quantity of nicotinamide, the quantity of pantothenic acid, the quantity of folic acid, the quantity of vitamin D3, and the quantity of pyridoxal 5-phosphate, as shown in FIG. 7. In accordance to Table 3, the preferred composition of the second quantity of additional vitamin supplement is as follows: the quantity of beta carotene is approximately 0.4% of the third medicinal mixture; the quantity of d-alpha tocopheryl succinate is approximately 1.4% of the third medicinal mixture; the quantity of thiamin is approximately 0.7% of the third medicinal mixture; the quantity of riboflavin is approximately 0.2% of the third medicinal mixture; the quantity of methylcobalamin is approximately 0.12% of the third medicinal mixture; the quantity of nicotinamide is approximately 1.34% of the third medicinal mixture; the quantity of pantothenic acid is approximately 0.2% of the third medicinal mixture; the quantity of folic acid is approximately 0.04% of the third medicinal mixture; the quantity of vitamin D3 is approximately 0.5% of the third medicinal mixture; and the quantity of pyridoxal 5-phosphate is approximately 0.08% of the third medicinal mixture. This composition provides these ingredients of the second quantity of additional vitamin supplements in sufficient quantity to be beneficial to the patient over the administration period for the third medicinal mixture.

In some embodiments of the present invention, a second quantity of additional dietary supplements is heterogeneously mixed into the third medicinal mixture, as shown in FIG. 2. In accordance to FIG. 7, the second quantity of dietary supplements is selected from a group consisting of: a quantity of potassium iodide, a quantity of calcium carbonate, a quantity of magnesium hydroxide, a quantity of magnesium gluconate, a quantity of copper gluconate, a quantity of zinc sulfate, a quantity of L-arginine, and combinations thereof. Similar to the first quantity of additional dietary supplements, the second quantity of additional dietary supplements provides essential nutrients to be metabolized by the patient. In one embodiment of the present invention, the second quantity of additional dietary supplements is a combination of the quantity of potassium iodide, the quantity of calcium carbonate, the quantity of magnesium hydroxide, the quantity of magnesium gluconate, the quantity of copper gluconate, the quantity of zinc sulfate, and the quantity of L-arginine. In accordance to Table 3, the composition for the second additional dietary supplement is as follows: the quantity of potassium iodide is approximately 0.27% of the third medicinal mixture; the quantity of calcium carbonate is approximately 3.1% of the third medicinal mixture; the quantity of magnesium hydroxide is approximately 3.8% of the third medicinal mixture; the quantity of magnesium gluconate is approximately 0.62% of the third medicinal mixture; the quantity of copper gluconate is approximately 0.08% of the third medicinal mixture; the quantity of zinc sulfate is approximately 1.35% of the third medicinal mixture; and the quantity of L-arginine is approximately 1.55% of the third medicinal mixture. This composition provides these ingredients for the second quantity of dietary supplements for a sufficient amount to be beneficial to the patient over the administration period for the third medicinal mixture.

Although the invention has been explained in relation to its preferred embodiment, it is to be understood that many other possible modifications and variations can be made without departing from the spirit and scope of the invention as hereinafter claimed.

What is claimed is:

1. A method for treating azoospermia comprises the steps of:
    providing a quantity of *glycyrrhiza glabra*, a quantity of red *panax ginseng*, a quantity of pomegranate, a quantity of maca, a quantity of *tribulus terrestris*, a quantity of horny goat weed, a quantity of *mucuna pruriens*, a quantity of damiana leaf, a quantity of *ginkgo biloba*, a quantity of grape seed extract, and a quantity of vitamin C;
    heterogeneously mixing a first portion of the quantity of *glycyrrhiza glabra* into a first medicinal mixture;
    heterogeneously mixing a second portion of the quantity of *glycyrrhiza glabra*, a first portion of the quantity of red *panax ginseng*, a first portion of the quantity of pomegranate, a first portion of the quantity of maca, and a first portion of the *tribulus terrestris* into a second medicinal mixture;
    heterogeneously mixing a third portion of the quantity of *glycyrrhiza glabra*, a second portion of the quantity of red *panax ginseng*, second a portion of the quantity of pomegranate, a second portion of the quantity of maca, a second portion of the *tribulus terrestris*, the quantity of horny goat weed, the quantity of *mucuna pruriens*, the quantity of damiana leaf, the quantity of *ginkgo biloba*, the quantity of grape seed extract, and the quantity of vitamin C into a third medicinal mixture;
    administering the first medicinal mixture to a patient daily for at least one month;
    subsequently administering the second medicinal mixture to the patient daily for at least two months; and
    subsequently administering the third medicinal mixture to the patient daily for at least three months.

2. The method for treating azoospermia, as claimed in claim 1, wherein the first medicinal mixture is a mass quantity between 10 milligrams (mg) and 1 gram (g).

3. The method for treating azoospermia, as claimed in claim 1, wherein the second medicinal mixture is a mass quantity between 10 mg and 1 g.

4. The method for treating azoospermia, as claimed in claim 1, wherein the third medicinal mixture is a mass quantity between 10 mg and 1 g.

5. The method for treating azoospermia, as claimed in claim 1, comprises:
    the first portion of the quantity of *glycyrrhiza glabra* being at least 96% by weight (wt %) of the first medicinal mixture.

6. The method for treating azoospermia, as claimed in claim 1, comprises:
    the second portion of the quantity of *glycyrrhiza glabra* being at least 60 wt % of the second medicinal mixture;
    the first portion of the quantity of red *panax ginseng* being at least 3 wt % of the second medicinal mixture;
    the first portion of the quantity of pomegranate being at least 10 wt % of the second medicinal mixture;
    the first portion of the quantity of maca being at least 3 wt % of the second medicinal mixture; and
    the first portion of the *tribulus terrestris* being at least 3 wt % of the second medicinal mixture.

7. The method for treating azoospermia, as claimed in claim 1, comprises:
    the third portion of the quantity of *glycyrrhiza glabra* being at least 10 wt % of the third medicinal mixture;
    the second portion of the quantity of red *panax ginseng* being at least 3 wt % of the third medicinal mixture;
    the second portion of the quantity of pomegranate being at least 5 wt % of the third medicinal mixture;
    the second portion of the quantity of maca being at least 10 wt % of the third medicinal mixture;
    the second portion of the *tribulus terrestris* being at least 3 wt % of the third medicinal mixture;
    the quantity of horny goat weed mixture being at least 5 wt % of the third medicinal mixture;
    the quantity of *mucuna pruriens* being at least 5 wt % of the third medicinal mixture;
    the quantity of damiana leaf being at least 5 wt % of the third medicinal mixture;
    the quantity of *ginkgo biloba* being at least 6 wt % of the third medicinal mixture;
    the quantity of grape seed extract being at least 10 wt % of the third medicinal mixture; and
    the quantity of vitamin C being at least 15 wt % of the third medicinal mixture.

8. The method for treating azoospermia, as claimed in claim 1, comprises the steps of:
    wherein a first quantity of additional vitamin supplements is selected from a group consisting of: a quantity of beta carotene, a quantity of d-alpha tocopheryl succinate, a quantity of thiamin, a quantity of riboflavin, a quantity of methylcobalamin, a quantity of nicotinamide, a quantity of pantothenic acid, a quantity of folic acid, and combinations thereof; and
    heterogeneously mixing the first quantity of additional vitamin supplements into the second medicinal mixture.

9. The method for treating azoospermia, as claimed in claim 8, comprises the steps of:
    wherein the first quantity of additional vitamin supplements is a combination of the quantity of beta carotene, the quantity of d-alpha tocopheryl succinate, the quantity of thiamin, the quantity of riboflavin, the quantity of methylcobalamin, the quantity of nicotinamide, the quantity of pantothenic acid, and the quantity of folic acid;
    the quantity of beta carotene being approximately 0.07% of the second medicinal mixture;
    the quantity of d-alpha tocopheryl succinate being approximately 0.1% of the second medicinal mixture;
    the quantity of thiamin being approximately 0.07% of the second medicinal mixture;
    the quantity of riboflavin being approximately 0.05% of the second medicinal mixture;
    the quantity of methylcobalamin being approximately 0.05% of the second medicinal mixture;
    the quantity of nicotinamide being approximately 0.5% of the second medicinal mixture;
    the quantity of pantothenic acid being approximately 0.05% of the second medicinal mixture; and
    the quantity of folic acid being approximately 0.03% of the second medicinal mixture.

10. The method for treating azoospermia, as claimed in claim 1, comprises the steps of:
    wherein a second quantity of additional vitamin supplements is selected from a group consisting of: a quantity of beta carotene, a quantity of vitamin D3, a quantity of d-alpha tocopheryl succinate, a quantity of thiamin, a quantity of riboflavin, a quantity of methylcobalamin, a quantity of nicotinamide, a quantity of pantothenic acid, a quantity of folic acid, a quantity of pyridoxal 5-phosphate, and combinations thereof; and heterogeneously mixing the second quantity of additional vitamin supplements into the third medicinal mixture.

11. The method for treating azoospermia, as claimed in claim 10, comprises the steps of:

wherein the second quantity of additional vitamin supplements is a combination of the quantity of beta carotene, the quantity of vitamin D3, the quantity of d-alpha tocopheryl succinate, the quantity of thiamin, the quantity of riboflavin, the quantity of methylcobalamin, the quantity of nicotinamide, the quantity of pantothenic acid, the quantity of folic acid, and the quantity of pyridoxal 5-phosphate;

the quantity of beta carotene being approximately 0.4% of the third medicinal mixture;

the quantity of vitamin D3 being approximately 0.5% of the third medicinal mixture;

the quantity of d-alpha tocopheryl succinate being approximately 1.4% of the third medicinal mixture;

the quantity of thiamin being approximately 0.7% of the third medicinal mixture;

the quantity of riboflavin being approximately 0.2% of the third medicinal mixture;

the quantity of methylcobalamin being approximately 0.12% of the third medicinal mixture;

the quantity of nicotinamide being approximately 1.34% of the third medicinal mixture;

the quantity of pantothenic acid being approximately 0.2% of the third medicinal mixture;

the quantity of folic acid being approximately 0.04% of the third medicinal mixture; and the quantity of pyridoxal 5-phosphate being approximately 0.08% of the third medicinal mixture.

12. The method for treating azoospermia, as claimed in claim 1, comprises the steps of:

wherein a first quantity of additional dietary supplements is selected from a group consisting of: a quantity of potassium iodide, a quantity of calcium carbonate, a quantity of magnesium hydroxide, a quantity of magnesium gluconate, and combinations thereof; and heterogeneously mixing the first quantity of additional dietary supplements into the second medicinal mixture.

13. The method for treating azoospermia, as claimed in claim 12, comprises the steps of:

wherein the first quantity of additional dietary supplements is a combination of the quantity of potassium iodide, the quantity of calcium carbonate, the quantity of magnesium hydroxide, and the quantity of magnesium gluconate;

the quantity of potassium iodide being approximately 0.14% of the second medicinal mixture;

the quantity of calcium carbonate being approximately 0.22% of the second medicinal mixture;

the quantity of magnesium hydroxide being approximately 0.45% of the second medicinal mixture; and the quantity of magnesium gluconate being approximately 0.18% of the second medicinal mixture.

14. The method for treating azoospermia, as claimed in claim 1, comprises the steps of:

wherein a second quantity of additional dietary supplements is selected from a group consisting of: a quantity of potassium iodide, a quantity of calcium carbonate, a quantity of magnesium hydroxide, a quantity of magnesium gluconate, a quantity of copper gluconate, a quantity of zinc sulfate, a quantity of L-arginine, and combinations thereof; and heterogeneously mixing the second quantity of additional dietary supplements into the third medicinal mixture.

15. The method for treating azoospermia, as claimed in claim 14, comprises the steps of:

wherein the second quantity of additional dietary supplements is a combination of the quantity of potassium iodide, the quantity of calcium carbonate, the quantity of magnesium hydroxide, the quantity of magnesium gluconate, the quantity of copper gluconate, the quantity of zinc sulfate, and the quantity of L-arginine;

the quantity of potassium iodide being approximately 0.27% of the third medicinal mixture;

the quantity of calcium carbonate being approximately 3.1% of the third medicinal mixture;

the quantity of magnesium hydroxide being approximately 3.8% of the third medicinal mixture;

the quantity of magnesium gluconate being approximately 0.62% of the third medicinal mixture;

the quantity of copper gluconate being approximately 0.08% of the third medicinal mixture;

the quantity of zinc sulfate being approximately 1.35% of the third medicinal mixture; and the quantity of L-arginine being approximately 1.55% of the third medicinal mixture.

* * * * *